US011383003B2

(12) United States Patent
Koenig et al.

(10) Patent No.: US 11,383,003 B2
(45) Date of Patent: *Jul. 12, 2022

(54) WATER SOLUBLE FARNESOL ANALOGS AND THEIR USE

(71) Applicant: Kimberly-Clark Worldwide, Inc., Neenah, WI (US)

(72) Inventors: David William Koenig, Menasha, WI (US); Mary Kay Foegen, Appleton, WI (US); Corey Thomas Cunningham, Larsen, WI (US); Aimin He, Atlanta, GA (US); Yang Huang, Jiangsu (CN)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/742,404

(22) Filed: Jan. 14, 2020

(65) Prior Publication Data

US 2020/0188551 A1 Jun. 18, 2020

Related U.S. Application Data

(63) Continuation of application No. 14/655,359, filed as application No. PCT/CN2012/087683 on Dec. 27, 2012, now Pat. No. 10,532,124.

(51) Int. Cl.
| | | |
|---|---|---|
| *A61L 15/44* | (2006.01) | |
| *C07C 69/67* | (2006.01) | |
| *C07C 69/73* | (2006.01) | |
| *C07C 43/178* | (2006.01) | |
| *C07H 3/02* | (2006.01) | |
| *A61L 15/20* | (2006.01) | |
| *A61F 13/84* | (2006.01) | |
| *C07C 69/40* | (2006.01) | |

(52) U.S. Cl.
CPC .......... *A61L 15/44* (2013.01); *A61F 13/8405* (2013.01); *A61L 15/20* (2013.01); *C07C 43/178* (2013.01); *C07C 43/1785* (2013.01); *C07C 69/40* (2013.01); *C07C 69/67* (2013.01); *C07C 69/73* (2013.01); *C07H 3/02* (2013.01); *A61L 2300/22* (2013.01); *A61L 2300/232* (2013.01); *A61L 2300/404* (2013.01)

(58) Field of Classification Search
None
See application file for complete search history.

(56) References Cited

U.S. PATENT DOCUMENTS

| | | | |
|---|---|---|---|
| 3,494,821 A | 2/1970 | Evans | |
| 3,665,040 A | 5/1972 | Ruegg et al. | |
| 4,100,324 A | 7/1978 | Anderson et al. | |
| 4,144,370 A | 3/1979 | Boulton | |
| 4,939,171 A | 7/1990 | Moeller et al. | |
| 5,057,361 A | 10/1991 | Sayovitz et al. | |
| 5,240,764 A | 8/1993 | Haid et al. | |
| 5,284,703 A | 2/1994 | Everhart et al. | |
| 5,312,814 A | 5/1994 | Biller et al. | |
| 5,350,624 A | 9/1994 | Georger et al. | |
| 5,783,171 A | 7/1998 | Gustavson et al. | |
| 5,785,179 A | 7/1998 | Buczwinski et al. | |
| 5,843,056 A | 12/1998 | Good et al. | |
| 5,855,999 A | 1/1999 | McCormick | |
| 5,879,341 A | 3/1999 | Odorzynski et al. | |
| 5,917,084 A | 6/1999 | Jiang | |
| 5,964,351 A | 10/1999 | Zander | |
| 6,030,331 A | 2/2000 | Zander | |
| 6,149,934 A | 11/2000 | Krzysik et al. | |
| 6,158,614 A | 12/2000 | Haines et al. | |
| 6,231,865 B1 | 5/2001 | Hsu et al. | |
| 6,269,969 B1 | 8/2001 | Huang et al. | |
| 6,269,970 B1 | 8/2001 | Huang et al. | |
| 6,271,267 B1 | 8/2001 | Matsuoka et al. | |
| 6,273,359 B1 | 8/2001 | Newman et al. | |
| 6,315,864 B2 | 11/2001 | Anderson et al. | |
| 6,383,543 B1 | 5/2002 | Reznik | |
| 6,586,461 B1 | 7/2003 | Gibbs | |
| 6,645,516 B2 | 11/2003 | Auberger et al. | |
| 6,656,168 B2 | 12/2003 | Braverman et al. | |
| 6,972,191 B2 | 12/2005 | Muramatsu et al. | |
| 7,258,878 B2 | 8/2007 | Greene et al. | |
| 7,270,975 B2 | 9/2007 | Sundstrom | |
| 7,786,239 B2 | 8/2010 | Petrovic et al. | |
| 8,076,286 B2 | 12/2011 | Schmidtchen et al. | |
| 8,153,746 B2 | 4/2012 | Petrovic et al. | |
| 8,158,166 B2 | 4/2012 | Van Beek | |
| 8,242,302 B2 | 8/2012 | Takata et al. | |

(Continued)

FOREIGN PATENT DOCUMENTS

| | | |
|---|---|---|
| DE | 2021228 A1 | 11/1970 |
| DE | 4033567 A1 | 4/1992 |

(Continued)

OTHER PUBLICATIONS

Abstract of Chinese Patent—CN102432433, May 2, 2012, 1 page.
Abstract of Japanese Patent—JP2009073831, Apr. 9, 2009, 2 pages.
Abstract of Article—Li et al., "Chemical Modification of Vegetable Oils," Synthetic Lubricants, vol. 35, No. 3, 2008, pp. 25-28.
Bonifait et al., "Synthesis and antimicrobial activity of geranyloxy- and farnesyloxy-acetophenone derivatives against oral pathogens", Fitoterapia, vol. 83, 2012, pp. 996-999.

(Continued)

*Primary Examiner* — David J Blanchard
*Assistant Examiner* — Sarah J Chickos
(74) *Attorney, Agent, or Firm* — Dority & Manning, P.A.

(57) ABSTRACT

Farnesol analogs, along with their related products (e.g., treatment compositions, wipes, absorbent articles, etc.) and their methods of formation, are provided. The farnesol analog includes a hydrophilic end group (e.g., a hydroxyl end group or a carboxylic acid end group) attached to farnesol via a covalent linkage (e.g., an ester group or an ether group).

24 Claims, 5 Drawing Sheets

(56) References Cited

U.S. PATENT DOCUMENTS

| | | |
|---|---|---|
| 8,268,964 B2 | 9/2012 | Scholler et al. |
| 8,486,376 B2 | 7/2013 | Friedman et al. |
| 2003/0224034 A1 | 12/2003 | Koenig |
| 2004/0110257 A1 | 6/2004 | Millis et al. |
| 2004/0266302 A1 | 12/2004 | DiSalvo et al. |
| 2005/0014730 A1 | 1/2005 | Carlson et al. |
| 2005/0019379 A1 | 1/2005 | Lange et al. |
| 2008/0069782 A1 | 3/2008 | Goodman et al. |
| 2008/0118580 A1 | 5/2008 | Bockmuhl et al. |
| 2008/0213191 A1 | 9/2008 | Scavone et al. |
| 2008/0299103 A1 | 12/2008 | George et al. |
| 2010/0063099 A1 | 3/2010 | Levin et al. |
| 2010/0217006 A1 | 8/2010 | Kamiya |
| 2010/0222606 A1 | 9/2010 | Ernst et al. |
| 2010/0331409 A1 | 12/2010 | Tsai et al. |
| 2011/0160688 A1 | 6/2011 | Warren |
| 2011/0203946 A1 | 8/2011 | McCloskey et al. |
| 2012/0141569 A1 | 6/2012 | Lee et al. |
| 2012/0141571 A1 | 6/2012 | Lee et al. |

FOREIGN PATENT DOCUMENTS

| | | |
|---|---|---|
| FR | 4055 M | 5/1966 |
| GB | 472624 | 9/1937 |
| GB | 2297557 A | 8/1996 |
| JP | H10316617 A | 12/1998 |
| WO | WO9218465 | 10/1992 |
| WO | WO9921008 | 4/1999 |
| WO | WO1999067809 A1 | 12/1999 |
| WO | WO03035093 A1 | 5/2003 |
| WO | WO2006087569 A2 | 8/2006 |
| WO | WO2008065370 A2 | 6/2008 |
| WO | WO2008065527 A2 | 6/2008 |
| WO | WO2008090440 A1 | 7/2008 |
| WO | WO2009046314 A2 | 4/2009 |
| WO | WO2009093007 A2 | 7/2009 |
| WO | WO2011143744 A1 | 11/2011 |
| WO | WO2012077001 A2 | 6/2012 |

OTHER PUBLICATIONS

Breger et al., "Antifungal Chemical Compounds Identified Using a *C. elegans* Pathogenicity Assay," *PLoS Pathogens*, vol. 3, Issue 2, Feb. 2007, pp. 0168-0178.

Da Costa et al., "Simple reduction of ethyl, isopropyl and benzyl aromatic ester to alcohols using sodium borohydride-methanol system," General Papers, *ARKIVOC*, 2006, pp. 128-133.

Duez et al., "Towards the synthesis of bisubstrate inhibitors of protein farnesyltransferase: Synthesis and biological evaluation of new farnesylpyrophosphate analogues", Bioorganic & Medicinal Chemistry, vol. 18, 2010, pp. 543-556.

El-Barghouthi et al., "Examining the potency of suggested inhibitors for the phosphatase activity of the human soluble epoxide hydrolase by molecular dynamics simulations" Journal of Molecular Structure: THEOCHEM, vol. 944, 2010, pp. 97-104.

Éparvier et al., "Cytotoxic farnesyl glycosides from Pittosporum pancheri", Phytochemistry, vol. 68, 2007, pp. 604-608.

Hornby et al., "Quorum Sensing in the Dimorphic Fungus *Candida albicans* Is Mediated by Farnesol," *Applied and Environmental Microbiology*, vol. 67, No. 7, Jul. 2001, pp. 2982-1992.

Hui et al., "Chemical composition of lavender essential oil and its antioxidant activity and inhibition against rhinitis related bacteria", African Journal of Microbiology Research, vol. 4(4), Feb. 18, 2010, pp. 309-313.

International Search Report for PCT/CN2012/087683 dated Sep. 19, 2013, 3 pages.

Kim et al. Inhibition Effect of New Farnesol Derivatives on All-Trans-Retinoic Acid Metabolism, Metabolism, vol. 50 No. 11 Nov. 2001, pp. 1356-1360.

Machine Translation of a Korean Patent—KR20110049574A, 25 pages.

Tampakakis et al., "A C. elegans-based, whole animal, in vivo screen for the identification of antifungal compounds," Nature Protocols, vol. 3, No. 12, 2008, pp. 1925-1931.

Wattanasin et al., "N-Hydroxyglycine Derivatives as Novel Inhibitors of Squalene Synthase", Bioorganic & Medicinal Chemistry Letters, vol. 7, No. 23, 1997, pp. 3039-3044.

WATER SOLUBLE FARNESOL ANALOGS AND THEIR USE

CROSS REFERENCE TO RELATED APPLICATION

This application is a continuation of U.S. Pat. No. 10,532,124, filed on Jun. 25, 2015 as U.S. patent application Ser. No. 14/655,359, which is the national stage entry of International Patent Application No. PCT/CN2012/087683 having a filing date of Dec. 27, 2012, the entire contents of which are incorporated herein by reference.

BACKGROUND OF THE INVENTION

Like other species of the genus Candida, Candida albicans is a diploid fungus that grows both as yeast and filamentous cells. More specifically, C. albicans is a dimorphic fungus, which has both a yeast-like growth habit and a filamentous form consisting of both hyphae and pseudohyphae. C. albicans exists as part of the normal microbial flora in humans, but can produce opportunistic infections ranging from topical infections such as oral thrush to life-threatening disseminated mycoses. In response to changes in its environment, C. albicans can transition from budding yeast to its filamentous morphology. The filamentous morphology is important for its virulence and causes both skin and mucosal infections. Quorum sensing has been identified as a phenomenon contributing to C. albicans' morphogenic transition from its conidial to filamentous form.

Quorum sensing systems have been found to coordinate virulence and biofilm development of pathogenic microorganisms. Manipulation of quorum sensing systems has been recently considered a promising strategy for developing antimicrobial agents since the manipulation of quorum sensing systems only inhibits the virulence but not the growth of microorganisms.

Farnesol is an acyclic sesquiterpene alcohol (a class of terpenes) that is naturally found in many different essential oils, including but not limited to citronella oil, neroli oil, cyclamen oil, lemon grass oil, tuberose oil, rose oil, musk oil, and balsam and tolu oil. Generally, farnesol is an acyclic sesquiterpene alcohol found as a colorless liquid. Farnesol is insoluble in water, but miscible with oils. Farnesol has been found to act as a quorum sensing inhibitor to decrease the rate that Candida albicans transitions from budding yeast to the filamentous form.

However, the practical use of farnesol as a quorum sensing inhibitor with respect to C. albicans is particularly difficult due to its insoluble nature in water. That is, it is difficult to apply farnesol to wipes or other materials for use, especially in a large-scale manufacturing environment. Additionally, it is difficult to incorporate farnesol within compositions (e.g., lotions) that can be used as a quorum sensing inhibitor, particularly when applied to the skin of a user.

As such, a need exists for a manner in which farnesol can be used as a quorum sensing inhibitor of C. albicans in a practical manner.

SUMMARY OF THE INVENTION

Farnesol analogs are generally provided, along with their related products (e.g., treatment compositions, wipes, absorbent articles, etc.). In one embodiment, the farnesol analog includes a hydrophilic end group (e.g., a hydroxyl end group or a carboxylic acid end group) attached to farnesol via a covalent linkage (e.g., an ester group or an ether group).

In one embodiment, the farnesol analog can have the structure:

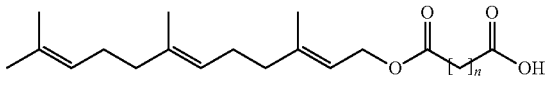

where n is an integer from 1 to about 8 (e.g., n is 2, 3, or 4), or its deprotonated salt.

The hydrophilic end group of the farnesol analog can, in one embodiment, comprises a second ester group. For example, the farnesol analog can have the structure:

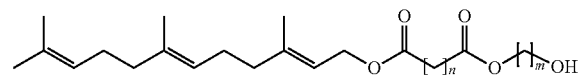

where n is an integer from 1 to about 8 (e.g., n is 2, 3, or 4); and m is an integer from 1 to about 8 (m is 2, 3, or 4).

In one particular embodiment, the covalent linkage of the farnesol analog can include an ether group, and the hydrophilic end group can be a hydroxyl end group. For example, the farnesol analog can have the structure:

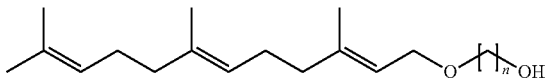

where n is an integer from 1 to about 8 (e.g., n is 2, 3, or 4). Alternatively, the farnesol analog can have the structure:

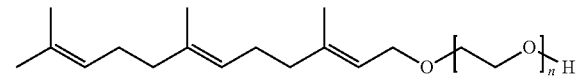

where n is an integer that is 1 to about 100. In yet another alternative embodiment, the farnesol analog can include a monosaccharide covalently attached to the farnesol via an ether linkage, such as the farnesol analog having the structure:

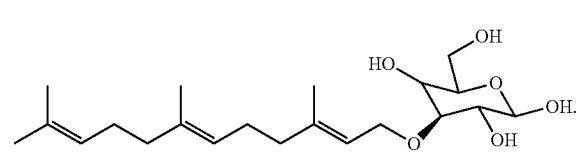

In one particular embodiment, the farnesol analog has a solubility in water that is 10 grams per 100 grams of water or greater.

Wipes are also generally provided that can include a web of a plurality of fibers and coated with a treatment composition that includes such a farnesol analog.

Absorbent articles are also generally provided that can include a liquid impermeable outer cover; a liquid permeable bodyside liner; an absorbent body disposed between the outer cover and bodyside liner; and a treatment composition applied to the bodyside liner. The treatment composition includes such a farnesol analog.

Methods are also generally provided for forming a farnesol analog that is soluble in water from a farnesol molecule having a hydroxyl group. The method can, in one embodiment, include covalently attaching a hydrophilic end group (e.g., a hydroxyl end group or a carboxylic acid end group) to the farnesol molecule via reaction with its hydroxyl group to form a covalent linkage (e.g., an ester group or an ether group).

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
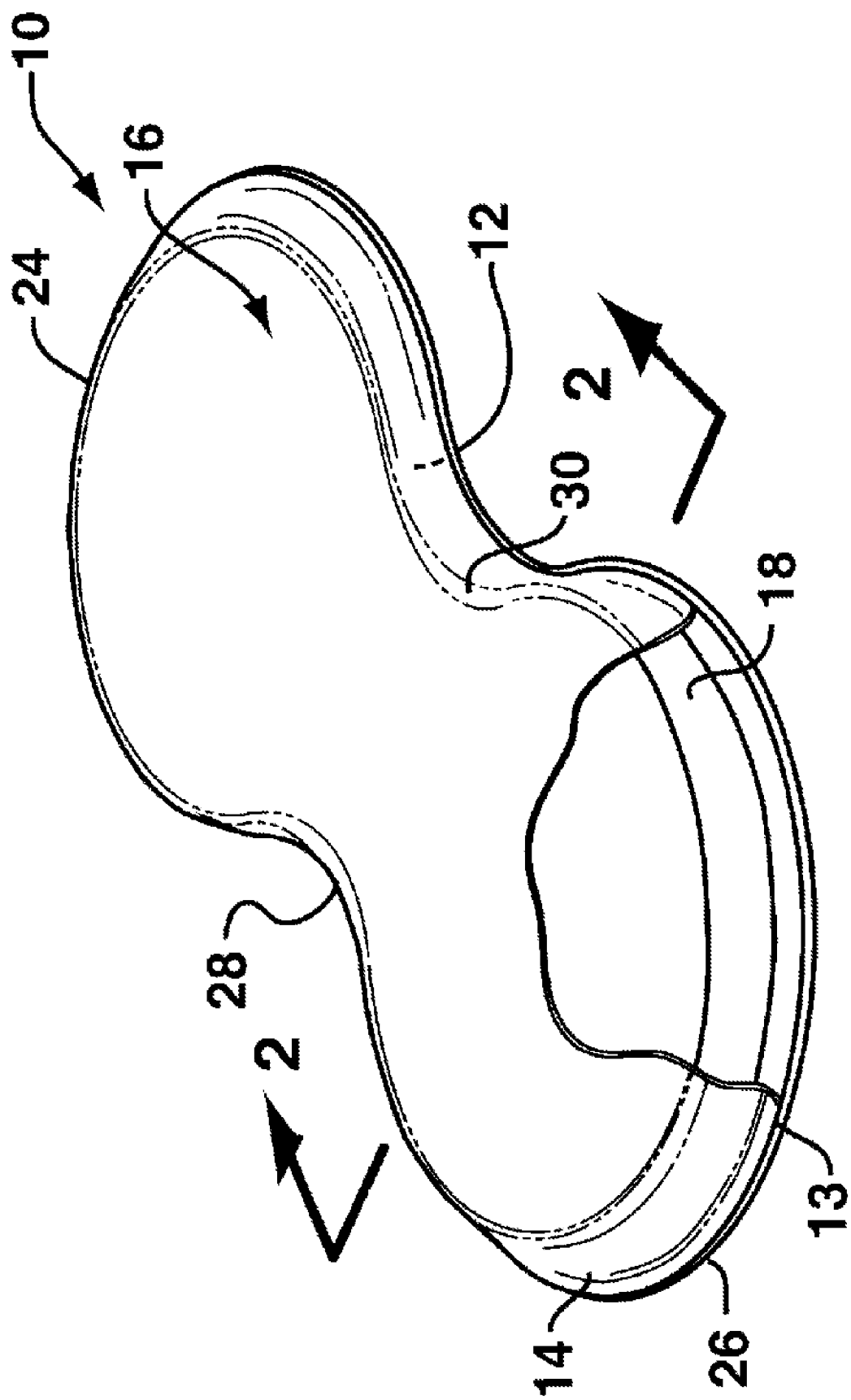
FIG. 1 is a perspective view of an exemplary feminine care absorbent article.

Repeat use of references characters in the present specification and drawings is intended to represent the same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Methods are generally provided for modifying farnesol to be more hydrophilic, along with the resulting farnesol analogs. Uses of such farnesol analogs are also generally provided in a treatment composition (e.g., a lotion) and as an additive to a wipe and/or an absorbent article. In one particular embodiment, the farnesol analogs can generally act as a quorum sensing inhibitor to decrease the rate that Candida albicans, and other species of the genus Candida, transitions from budding yeast to the filamentous form. Although referred to hereafter with respect to Candida albicans, the presently disclosed compositions, methods, and farnesol analogs are also applicable to other species of yeast within the genus Candida (e.g., C. glabrata, C. rugosa, C. parapsilosis, C. tropicalis, and C. dubliniensis, and C. oleophila).

Thus, the farnesol analogs can serve as an inhibitor of infection by Candida albicans on the skin of the user, when applied within a lotion, via a wipe, or when included on an absorbent article in a manner that can contact or be in close proximity to the skin of the wearer.

When applied to C. albicans, the farnesol analog can, in certain embodiments, have a percentage of cells with germ tubes formed (GTF %) of less than about 50%, such as less than about 25%.

I. Methods of Modifying Farnesol

Farnesol is a natural organic compound that is insoluble in water. It can be readily isolated from its natural sources (e.g., essential oils), or can be synthetically formed. Farnesol has the chemical structure shown below:

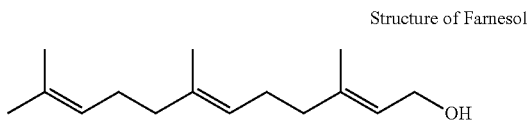 [SMILES: CC(C)=CCC/C(C)=C/CC/C(C)=C/CO]

Structure of Farnesol

Due to the presence of the hydroxyl end group (i.e., —OH), a hydrophilic end group can be readily attached through reaction of the hydroxyl group via any number of reactions suitable for aliphatic alcohols. For example, acid-base reactions, esterification reactions, etherification, substitution, elimination, etc. can be utilized to attach a hydrophilic end group onto the farnesol to form an analog.

By adding the polar, hydrophilic end groups, the farnesol analog becomes much more like a non-ionic surfactant comprised of a hydrophobic tail (the terpenoid chain) and a hydrophilic head group (the added end group). With this chemical structure, the farnseol analog is prone to acting like a surface active agent (surfactant) and can thus organize in micelles, bilayers, or any of the other known surfactant phases. While the modified oil is generally water soluble, micelles may form in the water solution. However, no separate phase is detected in the solution. For example, the farnesol analog can have a solubility in water of about 10 grams per 100 grams of water or greater due to the presence of the hydrophilic end group (e.g., a hydroxyl end group, a carboxylic acid end group, etc.) and/or a polar linkage (e.g., an ester, an ether, etc.).

A. Farnesol Analogs Having at Least One Ester Linkage

In one particular embodiment, a carboxylic acid functional molecule can be reacted with the hydroxyl end group of the farnesol molecule through an esterification reaction. As such, a hydrophilic end group can be attached to farnesol via an ester linkage (i.e., —COO—).

In addition to the carboxylic group, the carboxylic acid functional molecule can also include a hydrophilic chain. As such, following the esterification reaction, the hydrophilic chain is covalently attached to the components of the reactive product via an ester group and optionally an alkane chain (e.g., having 1 to about 8 carbon atoms, such as 1 to about 4 carbons).

In one particular embodiment, the carboxylic acid functional molecule is a dicarboxylic acid, such as oxalic acid, malonic acid, succinic acid, glutaric acid, adipic acid, pimelic acid, suberic acid, tartaric acid, etc. As such, following the esterification reaction, a carboxylic acid group is covalently attached to the farnesol via an ester group and an alkane chain (e.g., having 1 to about 8 carbon atoms, such as 1 to about 4 carbon atoms). Such a farnesol analog can be represented by the formula:

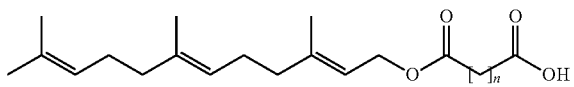

Formula 1 where n is 1 to about 8, such as 1 to 4 (e.g., 2, 3, or 4), along with their related deprotonated salts. For example, farnesol can be reacted with succinic acid through an esterification reaction (e.g., utilizing common esterification conditions such as acid catalysis, solid-supported acid catalysis like 1 mol % $HClO_4$—$SiO_2$, diethyl azodicarboxylate/triphenylphosphine (DEAD/$PPh_3$), dicyclohexylcarbodiimide/4-N,N-dimethylaminopyridine (DCC/DMAP), 4-(1-pyrrolidinyl)pyridine, or various Lewis acid catalysts) to form a farnesol analog having a carboxylic acid group covalently attached to the farnesol terpenoid chain via an ester group and an alkane chain of two carbon atoms, as shown in Farnesol Analog 1 represented below, which is intended to include its deprotonated salt:

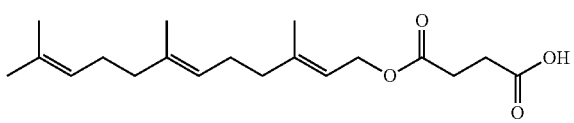

Exemplary Farnesol Analog 1

Exemplary Farnesol Analog 1 can then be rendered water soluble by raising the pH above the pKa of the Exemplary Farnesol Analog 1 to generate its deprotonated carboxylic salt.

Optionally, when the farnesol analog defines a carboxylic acid functional group (such as shown in Formula 1 and exemplary farnesol analog 1), a second esterification reaction with an alcohol can be utilized to form a second ester linkage to a hydrophilic end group. In one embodiment, a glycol can be reacted with the carboxylic acid functional farnesol analog (e.g., as in Formula 1) to attach a hydroxyl end group via a second ester linkage. Glycols refer generally to a class of organic compounds having two hydroxyl (—OH) groups attached to different carbon atoms. Particularly suitable glycols include, but are not limited to, ethylene glycol, propylene glycol, and butane-1,4-diol.

For example, an esterification reaction can be utilized to react the carboxylic acid functional farnesol analog shown in Formula 1 with a glycol to form a farnesol analog having a hydroxyl group covalently attached via two ester linkages, optionally a first alkane chain (e.g., having 1 to about 8 carbon atoms, such as 1 to about 4 carbon atoms), and optionally a second alkane chain (e.g., having 1 to about 4 carbon atoms, such as 2 or 3 carbon atoms). Such a farnesol analog can be represented by the formula, along with their deprotonated salts:

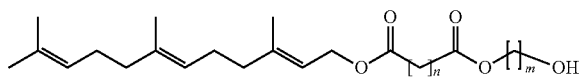

Formula 2 where n is 1 to about 8 (e.g., 1 to about 4) and m is 1 to about 8 (e.g., 2, 3, or 4). In particular embodiments, n can be 2 or 3 or 4 and m can be 2 or 3 or 4. For example, particularly suitable farnesol analogs having a hydroxyl end group attached via two ester linkages, a first alkane chain of 2 carbon atoms (i.e., n is 2), and a second alkane chain of 4, 3, and 2 carbon atoms are shown, respectively, below as the exemplary farnasol analogs 2, 3, and 4:

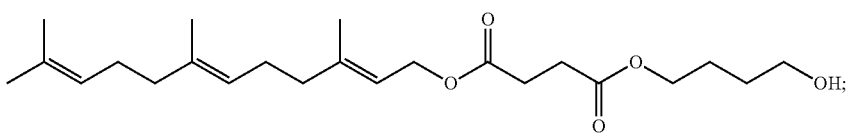

Exemplary Farnesol Analog 2

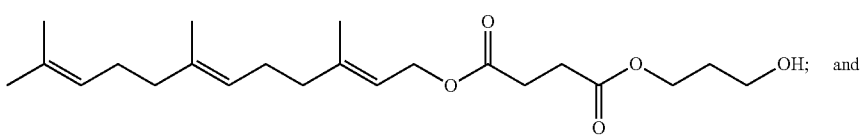

Exemplary Farnesol Analog 3 and

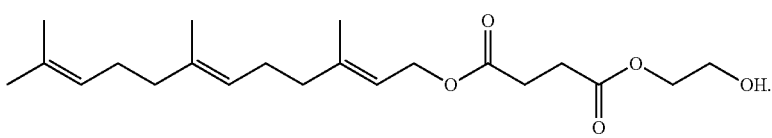

Exemplary Farnesol Analog 4

As such, in these embodiments, the hydrophilic end group contains at least one hydroxyl group (—OH) along the chain (e.g., a terminal hydroxyl group) and at least two ester linkages. Without wishing to be bound by any particular theory, it is believed that the presence of polar groups, such as hydroxyl group(s) and/or ester linkage(s), allows for the farnesol analog to be more soluble in water.

B. Farnesol Analogs Having a Carbonyl Linkage

In another embodiment, a hydrophilic end group can be covalently attached to the farnesol molecule through an ether linkage (i.e., —C—O—C—). For instance, the farnesol analog can have a hydrophilic group with a hydroxyl end group and an alkane chain having 1 to about 8 carbons (e.g., 1 to about 4 carbons) attached via an ether linkage. Such a farnesol analog can be represented by the formula, along with their deprotonated salts:

Formula 3

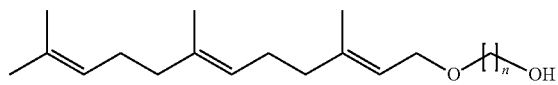

where n is 1 to about 8 (e.g., 2, 3, or 4).

In particular embodiments, n can be 2 or 3 or 4. For example, particularly suitable farnesol analogs having a hydroxyl end group attached via an ether linkage and an alkane chain of 4, 3, and 2 carbon atoms are shown, respectively, below as the exemplary farnasol analogs 5, 6, and 7:

Exemplary Farnesol Analog 5

Exemplary Farnesol Analog 6

Exemplary Farnesol Analog 7

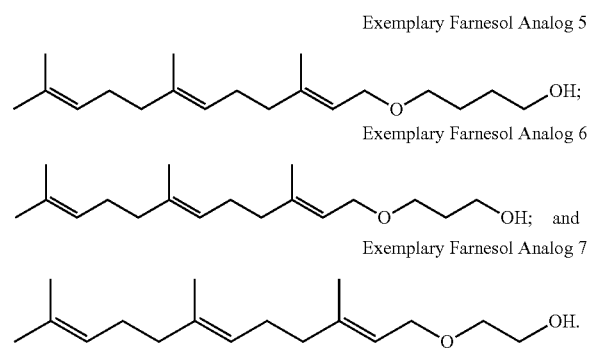

In one embodiment, for instance, farnesol can be reacted with another alcohol (e.g., a glycol) via a dehydration reaction to form an ether linkage to an alkane chain having a hydroxyl end group. For instance, a glycol (e.g., ethylene glycol, propylene glycol, etc.) can be reacted with the hydroxyl group of the farnesol to attach a hydroxyl end group via an ether linkage and an alkane chain having 1 to about 8 carbons (e.g., 1 to about 4 carbons), as shown in Formula 3 above. For example, particularly suitable dehydration reactions can be performed at elevated temperatures (e.g., about 125° C. or more), while catalyzed by an acid(s), such as sulfuric acid.

Other types of ether forming reactions can include so-called "Williamson ether synthesis," which involves treatment of farnesol with a strong base to replace the hydrogen of the hydroxyl group with a suitable cation forming an alkoxide analog of farnesol. Then, an appropriate aliphatic compound having a suitable leaving group (R-X) at one end and a hydroxyl group (—OH) at the other end of the chain (e.g., generally X—R—OH, where X is the leaving group and R represents an alkane chain of 1 to about 8 carbons, as discussed above with reference to n in Formula 3). Particularly suitable leaving groups (X) include halides (e.g., iodide, bromide, etc.), sulfonates, and the like.

As such, in these embodiments, the hydrophilic end group contains at least one hydroxyl group (—OH) along the chain (e.g., a terminal hydroxyl group) and at least one ether linkage. Without wishing to be bound by any particular theory, it is believed that the presence of polar groups, such as hydroxyl group(s) and/or ether linkage(s), allows for the farnesol analog to be more soluble in water.

Polyalkyleneoxide farnesol analogs can also be formed by treating an alkaline solution of farnesol with alkylene oxide (e.g., ethylene oxide gas) in the appropriate molar ratio depending on the desired length (or repeating units) of the alkylene oxide group. For example, the polyalkyleneoxide farnesol analog can be a polyethyleneoxide farnesol analog represented by the formula, along with the related deprotonated salts:

Exemplary Farnesol Analog 9

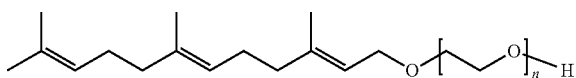

where n is an integer that is 1 to about 100 (e.g., 2 to about 20, such as 2 to about 5).

C. Attachment of a Sugar to Farnesol

In one embodiment, a sugar can be covalently attached to the farnesol, such as via an ether linkage. For example, the sugar can be a monosaccharide end group (e.g., glucose, fructose, galactose, xylose, ribose, etc) or a disaccharide end group (e.g., sucrose).

Such an analog can be formed, for example, via a two-step reaction: (1) converting the hydroxyl group of the farnesol to a halide via N-bromosuccinimide (NBS), (2) followed by a $SN_2$ displacement reaction of the protected sugar with the halogenated farnesol. The protecting groups are then removed from the sugar following standard protocols.

For example, exemplary farnesol analog 8 shows a glucose end group attached to the farnesol via an ether linkage:

Exemplary Farnesol Analog 8

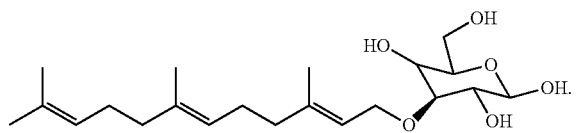

Such a farnesol analog, having a monosaccharide covalently attached to the farnesol via an ether linkage, defines a plurality of hydroxyl groups (—OH) and ether groups in its hydrophilic end group. This high concentration of polar groups can help increase the solubility of the farnesol analog in water.

II. Treatment Composition

The farnesol analog can be included within a treatment composition, which can be, for example, applied to the skin of a user. For example, the treatment composition may be administered to the skin of the user in a variety of forms, such as a lotion, cream, jelly, liniment, ointment, salve, oil, foam, gel, film, wash, coating, liquid, capsule, tablet, concentrate, etc.

The manner in which the treatment composition is formed may vary as is known to those skilled in the art. In one embodiment, for example, the farnesol analog may be initially blended with a solvent, such as water and/or an organic solvent. Organic solvents can be present, such as alcohols, such as methanol, ethanol, n-propanol, isopropanol, butanol, and so forth; triglycerides; ketones (e.g., acetone, methyl ethyl ketone, and methyl isobutyl ketone); esters (e.g., ethyl acetate, butyl acetate, diethylene glycol ether acetate, and methoxypropyl acetate); amides (e.g., dimethylformamide, dimethylacetamide, dimethylcaprylic/capric fatty acid amide and N-alkylpyrrolidones); nitriles (e.g., acetonitrile, propionitrile, butyronitrile and benzonitrile); sulfoxides or sulfones (e.g., dimethyl sulfoxide (DMSO) and sulfolane); and so forth. The combination of the ingredients may be facilitated through agitation (e.g., stirring) and control of the temperatures of each mixture. Conventional homogenization techniques may, for instance, be employed to stabilize the treatment composition.

The resulting treatment composition may contain a discontinuous oil phase dispersed within a continuous solvent phase. Nevertheless, due to the stability imparted by the hydrophilic end group on the farnesol analog, a relatively small amount of the farnesol analog may be employed and still achieve the desired quorum sensing inhibition of *C. albicans*. More particularly, the coating solution may employ farnesol analogs in an amount of from about 0.05 wt. % to about 15 wt. %, in some embodiments from about 0.1 wt. % to about 10 wt. %, and in some embodiments, from about 0.5 wt. % to about 5 wt %. For example, in one particular embodiment, the coating solution may employ farnesol analogs in a relatively small amount, while still achieving the desired quorum sensing inhibition, such as in an amount of from about 0.01 wt. % to about 1 wt. % (e.g., about 0.05 wt. % to about 0.5 wt. %).

Other additives may also be incorporated into the treatment composition. For example, the composition may contain a preservative or preservative system to inhibit the growth of microorganisms over an extended period of time. Suitable preservatives may include, for instance, alkanols, disodium EDTA (ethylenediamine tetraacetatic acid), EDTA salts, EDTA fatty acid conjugates, isothiazolinones, phenoxyethanol, phenethyl alcohol, caprylyl glycol, 1,2-hexanediol, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate). Another suitable preservative is Kathon CG®, which is a mixture of methylchloroisothiazolinone and methylisothiazolinone available from Dow Chemical; Mackstat H 66 (available from Rhodia, part of the Solvay Group). Still another suitable preservative system is a combination of 56% propylene glycol, 30% diazolidinyl urea, 11% methylparaben, and 3% propylparaben available under the name GERMABEN® II from Ashland.

The pH of the composition may also be controlled within a range that is considered more biocompatible. For instance, it is typically desired that the pH is within a range of from about 3 to about 9, in some embodiments from about 4 to about 8, and in some embodiments, from about 5 to about 7. Various pH modifiers may be utilized in the composition to achieve the desired pH level. Some examples of pH modifiers that may be used in the present invention include, but are not limited to, mineral acids, sulfonic acids (e.g., 2-[N-morpholino] ethane sulfonic acid), carboxylic acids, and polymeric acids. Specific examples of suitable mineral acids are hydrochloric acid, nitric acid, phosphoric acid, and sulfuric acid. Specific examples of suitable carboxylic acids are lactic acid, acetic acid, citric acid, glycolic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid. Basic pH modifiers may also be used in some embodiments of the present invention to provide a higher pH value. Suitable pH modifiers may include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium metasilicates; monoethanolamine; triethylamine; isopropanolamine; diethanolamine; and triethanolamine. When utilized, the pH modifier may be present in any effective amount needed to achieve the desired pH level.

To better enhance the benefits to consumers, other optional ingredients may also be used. For instance, some classes of ingredients that may be used include, but are not limited to: antioxidants (product integrity); anti-reddening agents, such as aloe extract; astringents—cosmetic (induce a tightening or tingling sensation on skin); colorants (impart color to the product); deodorants (reduce or eliminate unpleasant odor and protect against the formation of malodor on body surfaces, by, for example, absorption, adsorption, or masking); fragrances (consumer appeal); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); and viscosity modifiers (e.g., thickeners to increase viscosity).

III. Wipe

In one embodiment, the treatment composition can be applied to a wipe prior to use. Such wipes may be used to reduce microbial or viral populations on a hard surface (e.g., sink, table, counter, sign, and so forth) or surface on a user/patient (e.g., skin, mucosal membrane, such as in the mouth, nasal passage, vagina, the area surrounding the vaginal opening, etc., wound site, surgical site, and so forth). The wipe may provide an increased surface area to facilitate contact of the composition with microorganisms. In addition, the wipe may also serve other purposes, such as providing water absorption, barrier properties, etc. The wipe may also eliminate microorganisms through shear forces imparted to the surface.

The wipe may be formed from any of a variety of materials as are well known in the art. For example, the wipe can include a nonwoven fabric, woven fabric, knit fabric, wet-strength paper, or combinations/laminates thereof.

Materials and processes suitable for forming such substrate are well known to those skilled in the art. For instance, some examples of nonwoven fabrics that may be used as the wipe in the present disclosure include, but are not limited to, spunbonded webs (apertured or non-apertured), meltblown webs, bonded carded webs, air-laid webs, coform webs, hydraulically entangled webs, and the like. In addition, nonwoven fabrics can contain synthetic fibers (e.g., polyethylenes, polypropylenes, polyvinyl chlorides, polyvinylidene chlorides, polystyrenes, polyesters, polyamides, polyimides, etc.); cellulosic fibers (softwood pulp, hardwood pulp, thermomechanical pulp, etc.); or combinations thereof.

In one particular embodiment, the wipe includes a fibrous web that contains absorbent fibers. For example, the wipe may be a cellulose based paper product containing one or more paper webs, such as facial tissue, bath tissue, paper towels, napkins, and so forth. The paper product may be single-ply in which the web forming the product includes a single layer or is stratified (i.e., has multiple layers), or multiply, in which the webs forming the product may themselves be either single or multi-layered. Normally, the basis weight of such a paper product is less than about 120 grams per square meter ("gsm"), in some embodiments less than about 80 gsm, in some embodiments less than about 60 gsm, and in some embodiments, from about 10 to about 60 gsm.

Any of a variety of materials can also be used to form the paper web(s) of the product. For example, the material used to make the paper product may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, bamboo, algae, and so forth. In addition, in some instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; polyhydroxyalkanoate; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al., which is incorporated herein by reference. The relative percentages of such fibers may vary over a wide range depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference. Alternatively, the nonwoven composite may be formed by hydraulically entangling staple length fibers and/or filaments with high-pressure jet streams of water. Various techniques for hydraulically entangling fibers are generally disclosed, for example, in U.S. Pat. No. 3,494,821 to Evans and U.S. Pat. No. 4,144,370 to Boulton, which are incorporated herein by reference. Hydraulically entangled nonwoven composites of continuous filaments (e.g., spunbond web) and natural fibers (e.g., pulp) are disclosed, for example, in U.S. Pat. No. 5,284,703 to Everhart, et al. and U.S. Pat. No. 6,315,864 to Anderson, et al., which are incorporated herein by reference. Hydraulically entangled nonwoven composites of staple fiber blends (e.g., polyester and rayon) and natural fibers (e.g., pulp), also known as "spunlaced" fabrics, are described, for example, in U.S. Pat. No. 5,240,764 to Haid, et al., which is incorporated herein by reference.

Regardless of the materials or processes utilized to form the wipe, the basis weight of the wipe is typically from about 20 to about 200 gsm, and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein by reference.

The treatment composition may be impregnated into the wipe during its formation or simply coated onto all or a portion of a surface of the wipe using known techniques, such as printing, dipping, spraying, melt extruding, coating (e.g., solvent coating, powder coating, brush coating, etc.), foaming, and so forth. Due to the increased solubility in water, the farnesol analog allows the treatment composition to be more compatible for application to the wipe using such conventional coating techniques.

In one embodiment, for example, the coating is applied to the wipe by dipping, spraying, or printing. In one embodiment, a benefit can be achieved by applying the treatment composition in a film-like pattern that is discontinuous over the surface of the wipe. The pattern may, for example, cover only from about 5% to about 95%, in some embodiments from about 10% to about 90%, and in some embodiments, from about 20% to about 75% of a surface of the wipe. Such patterned application may have various benefits, including enhanced softness and drape, improved absorbency, etc.

If desired, the wipe may be dried at a certain temperature to drive the solvents from the solution and form a concentrate. Such concentrates generally have a very high stability in storage. To use the wipe, water or an aqueous solution may simply be added, thereby releasing the farnesol analog and optionally re-emulsifying the concentrate. Drying may be accomplished using any known technique, such as an oven, drying rolls (e.g., through-air drying, Yankee dryer), etc. The temperature at which the wipe is dried generally depends on the time period over which it is dried, but is typically at least about 20° C., and in some embodiments, from about 30° C. to about 100° C. Drying may occur either before or after the solution is applied to the wipe. The solvent content of the resulting concentrate is thus typically less than about 5 wt. %, in some embodiments less than about 2 wt. %, and in some embodiments, less about 1 wt. %.

The solids add-on level of the treatment composition is typically from about 2 to about 100%, in some embodiments from about 10% to about 80%, and in some embodiments, from about 15% to about 70%. The "solids add-on level" is determined by subtracting the weight of the untreated substrate from the weight of the treated substrate (after drying), dividing this calculated weight by the weight of the untreated substrate, and then multiplying by 100%. Lower add-on levels may provide optimum functionality of the substrate, while higher add-on levels may provide optimum antimicrobial efficacy. In such embodiments, the treatment composition typically contains farnesol analogs in an amount of from about 0.05 wt. % to about 50 wt. %, in some embodiments from about 1 wt. % to about 40 wt. %, and in some embodiments, from about 5 wt. % to about 30 wt. %.

In addition to being employed as a treatment composition, the farnesol analog may also be in the form of a liquid. This may be accomplished by simply not drying the solution after it is applied to the wipe. While the solids add-on level of such "wet wipes" generally remain within the ranges noted above, the total amount of the solution employed in such "wet wipes" (including any solvents) depends in part upon the type of wipe material utilized, the type of container used to store the wipes, the nature of the solution, and the desired end use of the wipes. Generally, however, each wet wipe contains from about 150 wt. % to about 600 wt. %, and desirably from about 300 wt. % to about 500 wt. % of the solution on the dry weight of the wipe.

In one embodiment, the liquid component of the wet wipe may include water, a surfactant or surfactant system, a preservative, an optional pH modifier (e.g., buffering agent), and the farnesol analog. For instance, the liquid component can be at least 95% by weight water (e.g., about 97.5% to about 99% by weight), about 0.25 to about 1.5% by weight of a surfactant(s) (e.g., sodium lauryl glucose carboxylate, lauryl glucoside, sodium lauroyl sarcosinate, a polysorbate surfactant such as polysorbate 20, or combinations thereof), about 0.05% to about 1.0% by weight of a preservative(s) (e.g., methylisothiazolinone, sodium benzoate, or mixtures thereof), up to about 1.5% by weight of a pH modifier (e.g., malic acid), and up to about 2.5% by weight of the farnesol analog (e.g., about 0.01% by weight to about 0.5% by weight).

The present inventors have discovered that the treatment composition including the farnesol analog may inhibit (e.g., reduce by a measurable amount or to prevent entirely) transition of *Candida albicans* from budding yeast to the filamentous form by serving as a quorum sensing inhibitor.

IV. Absorbent Articles

Figure 2:
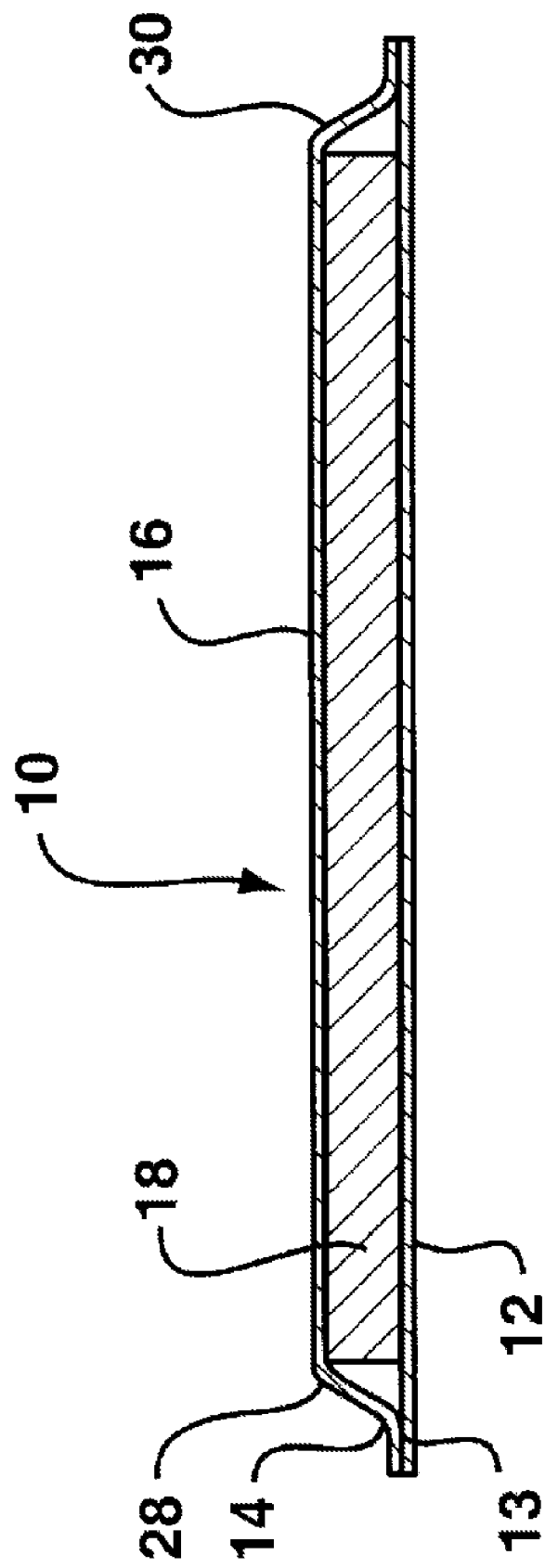
FIG. 2 is a cross-sectional view of the article of FIG. 1 taken along the lines indicated in FIG. 1.

Referring to FIGS. 1 and 2, a typical feminine care absorbent article 10, such as a pad or liner, is shown. The article 10 includes longitudinal ends 24 and 26 and opposed longitudinal sides 28 and 30, and is designed to extend through the wearer's crotch region between the legs upon the inside surface of an undergarment. FIG. 2 is a cut-away view of the article 10. In this view, it can be seen that the article 10 includes a substantially liquid impermeable outer cover 12, and an absorbent structure in superposed relation to the outer cover 12. The absorbent structure may include various layers and/or components. The topmost component defines a bodyfacing surface 16 that is disposed against the wearer's skin. In the illustrated embodiment, the absorbent structure includes a porous, liquid permeable bodyside liner 14 defining the bodyfacing surface 16, and an absorbent body 18, such as an absorbent pad, disposed between the outer cover 12 and bodyside liner 14. The bodyside liner 14 is generally superimposed and coextensive with the outer cover 12, but may cover an area which is larger or smaller than the area of the outer cover 12. The body side liner 14, outer cover 12, and absorbent body 18 are integrally assembled together employing suitable attachment means, such as adhesive, ultrasonic bonds, thermal bonds, etc. In the shown embodiment, the bodyside liner 14 and outer cover 12 are bonded together and to the absorbent body 18 with an adhesive, such as a hot melt, pressure-sensitive adhesive. The bodyside liner 14 is bonded to the outer cover 12 around the periphery of the article 10 to form a periphery margin area 13. In other embodiments, the outer cover 12 and bodyside liner 14 may have a periphery that is continuous with the edge of the absorbent body 18.

The outer cover 12 is desirably formed of a breathable material which permits vapors to escape from the absorbent body 18 while still preventing liquid exudates from passing through the outer cover 12. For example, in one particular embodiment, the outer cover 12 is formed by a microporous film/nonwoven laminate including a spunbond nonwoven material laminated to a microporous film. Suitable materials for the outer cover 12 are well known to those skilled in the art and many such materials are described, for example, in detail in U.S. Pat. No. 6,149,934 of Krzysik, et al., which is incorporated by reference herein. Reference is also made to U.S. Pat. No. 5,879,341 of Odorzynski, et al.; U.S. Pat. No. 5,843,056 of Good, et al.; and U.S. Pat. No. 5,855,999 of McCormack, which are incorporated by reference herein, for descriptions of suitable breathable materials for the outer cover 12.

The bodyside liner 14 presents the bodyfacing surface 16 which is compliant, soft, and nonirritating to the wearer's skin. The bodyside liner 14 helps to isolate the wearer's skin from liquids held in the absorbent body 18. Further, the bodyside liner 14 may be less hydrophilic than the absorbent body 18 to present a relatively dry surface to the wearer, and may be sufficiently porous to be liquid permeable so that liquid readily penetrates its thickness to be absorbed by the absorbent body 18. A suitable bodyside liner 14 may be made from a wide selection of materials, such as porous foams, reticulated foams, apertured plastic films, natural fibers, synthetic fibers, or any combination thereof. Various woven and nonwoven fabrics can be used for the bodyside liner 14. For example, the liner 14 may be composed of a meltblown or spunbonded web of polyolefin fibers. The bodyside liner 14 may also be a bonded-carded web of natural and/or synthetic fibers. The liner may be composed of a substantially hydrophobic material which, optionally, may be treated with a surfactant, a wetting agent, or otherwise processed to impart a desired level of wettability and hydrophilicity. The liner can be treated with a surfactant that includes a skin wellness treatment. This treatment can be applied in conjunction with a surfactant(s) or as a separate treatment.

The absorbent body 18 may comprise a matrix of hydrophilic fibers, such as a web of cellulosic fluff, alone or mixed with particles of a high-absorbency material commonly known as "superabsorbent material." The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may be selectively placed into desired zones of the absorbent body 18 to better contain and absorb body exudates. Alternatively, the absorbent body 18 may include a laminate of fibrous webs and/or fibrous webs and superabsorbent materials or other suitable means of maintaining a superabsorbent material in a localized area.

The high absorbency material can be selected from natural, synthetic, and modified natural polymers and materials. The high absorbency materials can be inorganic materials, such as silica gels, or organic compounds, such as cross-linked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly (vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body.

A hydrophilic wrap sheet may be employed to help maintain the structural integrity of the absorbent body 18. For example, the hydrophilic wrap sheet may be a tissue wrap sheet, a nonwoven wrap sheet, a nonwoven laminate wrap sheet, etc. The wrap sheet is typically placed about the absorbent body over at least two major facing surfaces thereof and composed of an absorbent cellulosic material, such as creped wadding or a high wet-strength tissue. The wrap sheet can be configured to provide a wicking layer which helps to rapidly distribute liquid over the mass of absorbent fibers constituting the absorbent body 18. Another layer or layers can be incorporated between the liner 14 and the absorbent body 18, such as a surge layer and/or transfer layer, etc.

According to embodiments of the present invention, the treatment composition can be included on or within the absorbent article 10, particularly on areas of the article 10 that may come into close proximity to the skin of the wearer. For example, the treatment composition can be applied on or within the bodyfacing surface 16 of the bodyside liner 14, such as by using the application techniques discussed above with reference to wipes.

In one embodiment, the treatment composition can be applied substantially uniformly on the entire bodyfacing surface 16. Alternatively, the treatment composition can be applied as discrete localized deposits on the bodyfacing surface 16 of the article, which may be, for example, the bodyfacing surface 16 of the bodyside liner 14, as discussed in greater detail below. It should be appreciated that the invention is not limited to an article having a bodyside liner 14. For example, in certain embodiments, the article may not include a liner 14 and the bodyfacing surface may be defined by an absorbent layer of material. In this case, the treatment composition would be directly applied on or within the absorbent layer, the surge layer, and/or the transfer layer (if present).

The amount of treatment composition may vary widely within the scope of the invention. For example, if a bodyside liner is used, it may be desired that the treatment composition be present at an add-on weight of between about 0.5% to about 50% of the weight of the bodyside liner 14. It is desired that the treatment composition remain substantially on the bodyfacing surface 16 where it can contact and/or transfer to the wearer's skin to provide the desired skin health benefit.

The treatment composition may be in addition to an overall skin wellness treatment applied uniformly to the bodyside liner 14. For example, the liner 14 may be treated with a surfactant that includes a skin wellness additive, or a skin wellness additive may be applied in an additional process. Any of the skin wellness additives discussed herein with respect to the treatment composition may be applied as a separate overall treatment to the liner 14.

The invention is not limited to any particular treatment composition. The treatment composition may include any combination of emollients, and may also include one or more waxes. A viscosity enhancer may also be included. The treatment composition may include other ingredients as well.

The emollients act as lubricants to reduce the abrasiveness of the bodyside liner to the skin and, upon transfer to the skin, help to maintain the soft, smooth and pliable appearance of the skin. Suitable emollients which can be incorporated into the treatment composition include oils such as petroleum based oils, vegetable based oils, mineral oils, natural or synthetic oils, silicone oils, lanolin and lanolin derivatives, kaolin and kaolin derivatives and the like and mixtures thereof; esters such as cetyl palmitate, stearyl palmitate, cetyl stearate, isopropyl laurate, isopropyl myristate, isopropyl palm itate and the like and mixtures thereof; glycerol esters; ethers such as eucalyptol, cetearyl glucoside, dimethyl isosorbicide polyglyceryl-3 cetyl ether, polyglyceryl-3 decyltetradecanol, propylene glycol myristyl ether and the like and mixtures thereof; alkoxylated carboxylic acids; alkoxylated alcohols; fatty alcohols such as octyldodecanol, lauryl, myristyl, cetyl, stearyl and behenyl alcohol and the like and mixtures thereof. For example, a particularly well suited emollient is petrolatum. Other conventional emollients may also be added in a manner which maintains the desired properties of the treatment composition set forth herein.

To provide the improved stability and transfer to the skin of the wearer, the treatment composition may include from about 5 to about 95 weight percent, desirably from about 20 to about 75 weight percent, and more desirably from about 40 to about 60 weight percent of the emollient.

The wax in the treatment composition, when included, can primarily function as an immobilizing agent for the emollient and any active ingredient. In addition to immobilizing the emollient and reducing its tendency to migrate, the wax in the treatment composition provides a tackiness to the lotion formulation which improves the transfer to the skin of the wearer. The presence of the wax also modifies the mode of transfer in that the treatment composition tends to fracture or flake off instead of actually rubbing off onto the skin of the wearer which can lead to improved transfer to the skin. The wax may further function as an emollient, occlusive agent, moisturizer, barrier enhancer and combinations thereof.

Suitable waxes which can be incorporated into the lotion formulation include animal, vegetable, mineral or silicone based waxes which may be natural or synthetic such as, for example, bayberry wax, beeswax, C30 alkyl dimethicone, candelilla wax, carnauba, ceresin, cetyl esters, esparto, hydrogenated cottonseed oil, hydrogenated jojoba oil, hydrogenated jojoba wax, hydrogenated microcrystalline wax, hydrogenated rice bran wax, Japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnauba wax, synthetic Japan wax, synthetic jojoba wax, synthetic wax, and the like and mixtures thereof. For example, a particularly well suited wax includes about 70 weight percent ceresin wax, about 10 weight percent microcrystalline wax, about 10 weight percent paraffin wax and about 10 weight percent cetyl esters (synthetic spermaceti wax).

To provide the improved transfer to the skin of the wearer, the treatment composition may include from about 5 to about 95 weight percent, desirably from about 25 to about 75 weight percent, and more desirably from about 40 to about 60 weight percent of the wax. Treatment compositions, which include an amount of wax less than the recited amounts, tend to have lower viscosities which undesirably leads to migration of the lotion. Whereas, treatment compositions which include an amount of wax greater than the recited amounts tend to provide less transfer to the wearer's skin.

A viscosity enhancer may be added to the treatment composition to increase the viscosity to help stabilize the formulation on the bodyfacing surface 16 of the bodyside liner 14 and thereby reduce migration and improve transfer to the skin. Desirably, the viscosity enhancer increases the viscosity of the treatment composition by at least about 50 percent, more desirably at least about 100 percent, even more desirably by at least about 500 percent, yet even more desirably by at least about 1000 percent, and even more desirably by at least about 5000 percent. Suitable viscosity enhancers which can be incorporated into the treatment composition include polyolefin resins, lipophilic/oil thickeners, ethylene/vinyl acetate copolymers, polyethylene, silica, talc, colloidal silicone dioxide, zinc stearate, cetyl hydroxy ethyl cellulose and other modified celluloses and the like and mixtures thereof.

To provide the improved transfer to the skin of the wearer, the treatment composition may include from about 0.1 to about 25 weight percent, desirably from about 5 to about 20 weight percent, and more desirably from about 10 to about 15 weight percent of the viscosity enhancer for reduced migration and improved transfer to the wearer's skin.

If it is desired that the treatment composition treat the skin, it can also include an active ingredient such as a skin protectant. Skin protectants may be a drug product which protects injured or exposed skin or mucous membrane surface from harmful or irritating stimuli. Suitable active ingredients, in addition to those mentioned above as suitable emollients, which can be incorporated into the lotion formulation include, but are not limited to, allantoin and its derivatives, aluminum hydroxide gel, calamine, cocoa butter, dimethicone, cod liver oil, glycerin, kaolin and its derivatives, lanolin and its derivatives, mineral oil, shark liver oil, talc, topical starch, zinc acetate, zinc carbonate, and zinc oxide and the like, and mixtures thereof. The treatment composition may include from about 0.10 to about 95 weight percent of the active ingredient depending upon the skin protectant and the amount desired to be transferred to the skin.

In order to better enhance the benefits to the wearer, additional ingredients can be included in the treatment composition. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); astringents—cosmetic (induce a tightening or tingling sensation on skin); astringent—drug (a drug product which checks oozing, discharge, or bleeding when applied to skin or a mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors); film formers (to hold active ingredients on the skin by producing a continuous film on skin upon drying); fragrances (consumer appeal), silicones/organomodified silicones (protection, tissue water resistance, lubricity, tissue softness), oils (mineral, vegetable, and animal); natural moisturizing agents or natural moisturizing factors (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics); and surfactants (as cleansing agents, emulsifying agents, solubilizing agents, and suspending agents).

The present invention may be better understood with reference to the following examples.

EXAMPLES

In vitro models were developed for screening quorum sensing inhibitory compounds/products against *Candida albicans* SC5314 to identify potential quorum sensing inhibitors. Potential quorum sensing inhibitory compounds/products were not only sourced from commercial analogs of quorum sensing molecules, natural antifungal botanicals and antifungal drugs, but also by synthesizing the analogs of farnesol and developing water soluble products.

Generally, these Examples presented the following key findings:

1. An in vitro model was established for screening quorum sensing inhibitory compounds against *C. albicans* SC5314;
2. Eight farnesol analogs were synthesized and screened by the in vitro model;
4. An in vitro model was established for screening quorum sensing inhibitory compounds against *C. albicans* SC 5314; and
5. Two synthesized farnesol analogs (#1 and #2) significantly reduced the death rate of *Caenorhabditis elegans* glp4; sek1 4 infected with *C. albicans* SC 5314.

Test Methods

In these examples, the YPD agar consisted of 10.0 g of peptone, 5.0 g of Yeast extract, 10.0 g of glucose, 10.0 g of agar, and 1.0 L of deionized water, which was prepared by mixing all ingredients and then sterilizing via autoclave at 115° C. for 30 min.

The YPD broth consisted of 10.0 g of peptone, 5.0 g of Yeast extract, 10.0 g of glucose, and 1.0 L of deionized water, which was prepared by mixing all ingredients and then sterilizing via autoclave at 115° C. for 30 min.

The mGSB broth consisted of 1.0 g of peptone, 2.0 g of $KH_2PO_4$, 1.0 g of $(NH_4)_2SO_4$, 0.05 g of $MgSO_4$, 0.05 g $CaCl_2 \cdot 2H_2O$, and 1.0 L of deionized water, which was prepared by mixing all ingredients and then sterilizing via autoclave at 121° C. for 15 min. After cool down, a filter sterilized 30 ml 50% glucose solution (w/v) and 0.4 ml GPP vitamin stock was added, which contained the following (per 100 ml of 20% ethanol): 2 mg of biotin, 20 mg of thiamine-HCl, and 20 mg of pyridoxine-HCl.

The NGM agar consisted of 2.5 g of peptone, 3.0 g of NaCl, 17 g of agar, and 975 mL of deionized water, which was prepared by mixing all ingredients and then sterilizing by autoclave at 121° C. for 15 min. After cool down, sterilized 25 ml of $KPO_4$ buffer (400 mM $KH_2PO_4$ and 100 mM $K_2HPO_4$), 0.1% 1 M $MgSO_4$ (v/v), 0.1% 1 M $CaCl_2$ (v/v), filter sterilized 100 mg/ml streptomycin, and 0.1% 5 mg/ml cholesterol in ethanol (v/v) were added.

The M9 buffer consisted of 3.0 g of $KH_2PO_4$, 6.0 g of $Na_2HPO_4$, 5.0 g of NaCl, and 1 L of deionized water, which was prepared by mixing all ingredients and then sterilizing by autoclave at 121° C. for 15 min. After cool down, 1 mL of filter sterilized 1 M $MgSO_4$ was added.

1. Development of In Vitro Screening Model a) Develop Protocols for Preparation of Single Cell Suspensions of *C. albicans*

Figure 3:
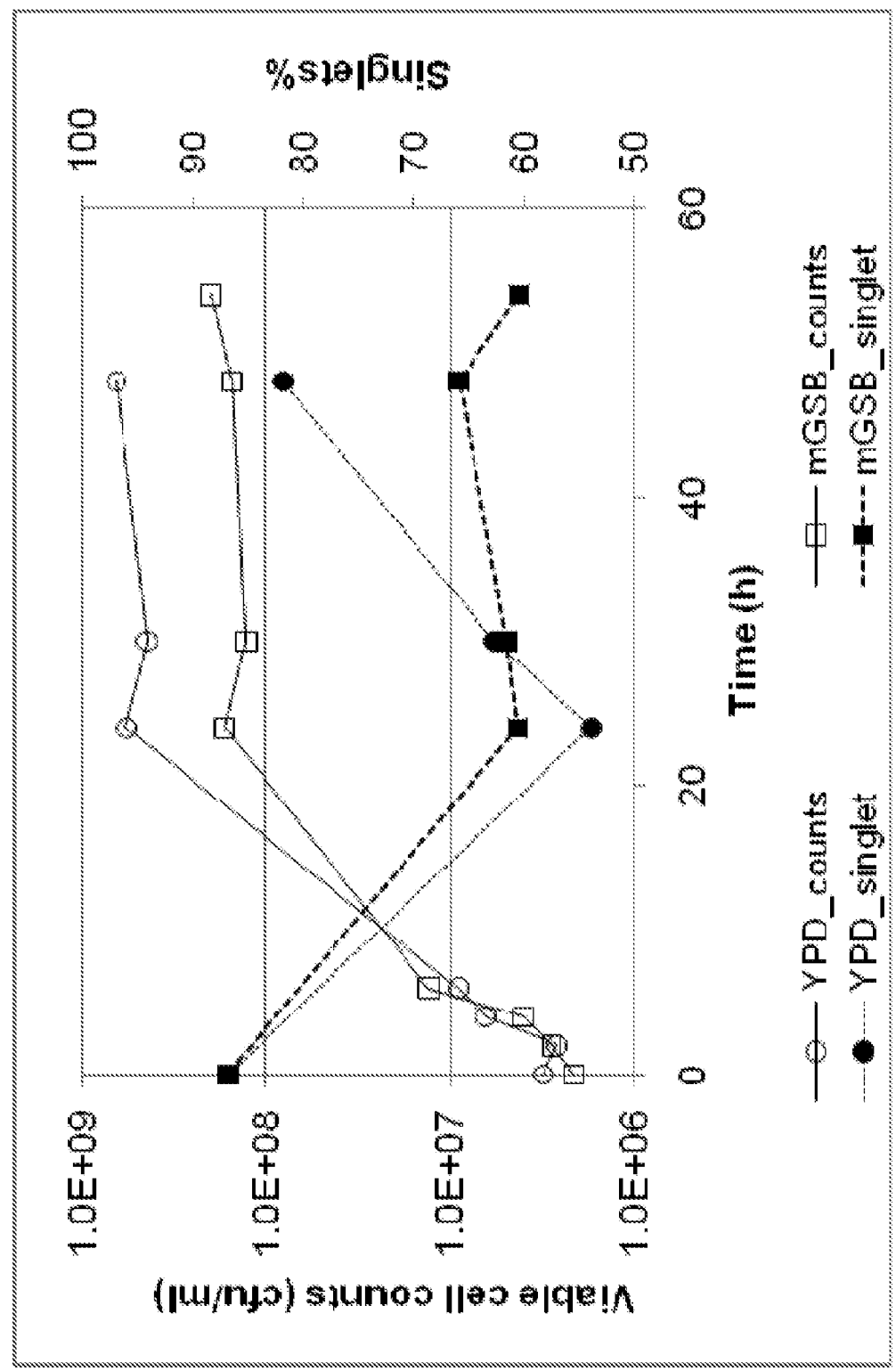
FIG. 3 shows a graph of the growth and percentage of singlet cells of C. albicans SC5314 in YPD and mGSB broths incubated at 30° C. according to the Examples.

The growth of *Candida albicans* SC5314 in two media, Yeast Extract Peptone Dextrose broth (commonly known as YPD broth), and modified glucose salts biotin broth (commonly known as mGSB broth), was examined during incubation at 30° C. FIG. 3 shows that SC5314 reached stationary phase after 24 h incubation at 30° C. in both media. The percentage of singlet cells decreased initially, and then increased after 24 h in both media. The percentage of singlet cells in YPD broth exceeded 80% after 48 h; whereas that in mGSB broth was around 60-70% after 30 h-54 h incubation.

Based on the results in FIG. 3, single cell suspensions of SC5314 was prepared as follows. Stock culture of *C. albicans* SC5314 was streaked onto YPD agar (YPDA) and incubated at 30° C. overnight. Single colonies were subcultured in YPD broth (YPDB) and incubated 30° C., 200 rpm overnight. Overnight culture in YPDB was subcultured in YPD broth again and incubated 30° C., 200 rpm 48 h. Cells were collected by centrifugation (4000 g 10 min) at 4° C., washed three times with sterile water, and then resuspended in sterile water a final concentration of $10^9$ colony-forming unit/ml (cfu/ml). The suspension were stored at 4° C. at least 1 d, then subcultured into YPDB to a final concentration of $10^6$ cfu/ml. After 48 h incubation, cell suspension was examined under the microscope for single cell percentage. When the single cell percentage exceeded 80%, cells were collected and washed three times with water, then resuspended in water to a final concentration of $10^9$ cfu/ml, and stored at 4° C. for no more than a month.

b) Develop Protocols for Determination of the Percentage of Germ Tubes Formed (GTF %)

Germinated yeast cells generally tend to aggregate, making it difficult to count the total number of cells during the in vitro screening. To disaggregate the cells, various approaches were attempted, such as vortexing with glass beads, sonication, addition of dithiothreitol (0.1 mM to 0.4 mM) and glutathione (reduced, 5 mM to 25 mM), and storage at various temperatures (4° C., 15° C., 20° C., 25° C.). Good disaggregation was observed only for storage at 15° C. for 20 h, as seen microscopically.

Two approaches were taken to determine the percentage of cells with germ tubes formed (GTF %). One way was to count the total cells at the start of incubation, and count the ungerminated cells after incubation, then calculate the GTF % as (1—ungerminated cells/total cells at 0 h)*100. Another way was to store the samples at 15° C. for 20 h after incubation, then count the germinated cells and total cells after disaggregation, then calculated the GTF % as (germinated cells/total cells after storage)*100. No significant difference was observed for the GTF % of C. albicans in a screening medium (11 mM imidazole buffer, 3 mM MgSO$_4$, and 2.6 mM N-acetyl-D-glucosamine) determined by the two methods. Therefore, for practical purposes, the GTF % was determined by the first method, that is, GTF %=(1—ungerminated cells/total cells at 0 h)*100, for the in vitro screening discussed herein.

c) Select Screening Media for In Vitro Screening

A screening medium, containing 11 mM imidazole buffer, 3 mM MgSO4, and 2.6 mM N-acetyl-D-glucosamine (GlcNAc) has been used to study the effect of farnesol analogs on the germ tube formation of C. albicans. Here, the germ tube formation of C. albicans in modified screening media was assessed with various concentrations of imidazole buffer (10 mM, 30 mM and 50 mM) and MgSO4 (0.5 mM, 1.5 mM and 3 mM). Table 1 shows that the GTF % deceased as the concentration of imidazole buffer increased; whereas the GTF % increased as the concentration of MgSO4 increased. It took 2 h to 3 h for the GTF % to reach above 80%. For practical purposes, the screening medium, containing 11 mM imidazole buffer, 0.5 mM MgSO4, and 2.6 mM N-acetyl-D-glucosamine (GlcNAc) was adopted for in vitro screening the quorum sensing inhibitory effect of farnesol compounds.

Table 1 shows the effect of concentrations of imidazole buffer and MgSO4 on the germ tube formation (GTF %) of C. albicans cells at 37° C. in screening media (pH 6.5) with 2.6 mM N-acetyl-D-glucosamine.

TABLE 1

| Imidazole | | GTF % | | | |
|---|---|---|---|---|---|
| buffer | Mg$^{2+}$ | 1.5 h | 2 h | 2.5 h | 3 h |
| 10 mM | 0.5 mM | 32.0 | 84.8 | | |
| | 1.5 mM | 34.4 | 88.8 | | |
| | 3.0 mM | 38.0 | 86.8 | | |
| 30 mM | 0.5 mM | 29.2 | 54.8 | 82.8 | |
| | 1.5 mM | 39.2 | 66.8 | 84.4 | |
| | 3.0 mM | 34.0 | 64.0 | 92.4 | |
| 50 mM | 0.5 mM | 18.8 | 38.4 | 65.2 | 76.4 |
| | 1.5 mM | 22.8 | 41.2 | 66.8 | 80.0 |
| | 3.0 mM | 10.0 | 62.0 | 68.8 | 85.6 |

Note:
GTF % was calculated as the 1-(ungerminated cells/total cells at 0 h)% d) Effect of Quorum Sensing Molecules on Lag Phase of C. albicans

Figure 4:
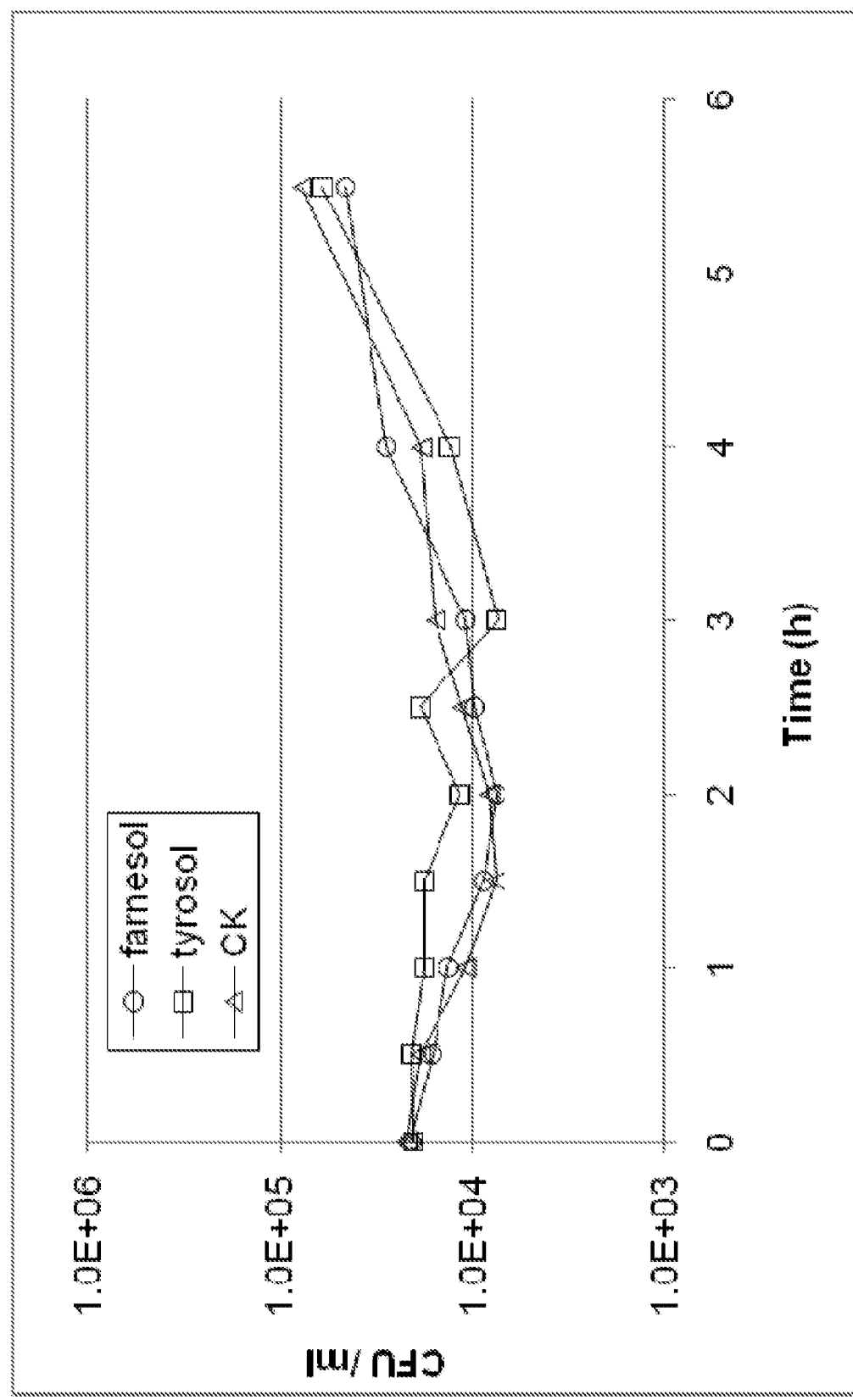
FIG. 4 shows the effect of farnesol (100 µM) and tyrosol (100 µM) on the lag phase of C. albicans SC5314 in YPD medium at 37° C. according to the Examples.

FIG. 4 shows that 100 μM farnesol or 100 μM tyrosol had little effect on the growth of C. albicans SC5314 in YPD broth at 37° C. for 6 h (where "CK" is a control sample of C. albicans SC5314 in YPD broth at 37° C. for 6 h). Those results confirm no increase of cells occurred during the period of the in vitro screening.

Synthesis of Farnesol Analogs

Figure 5:
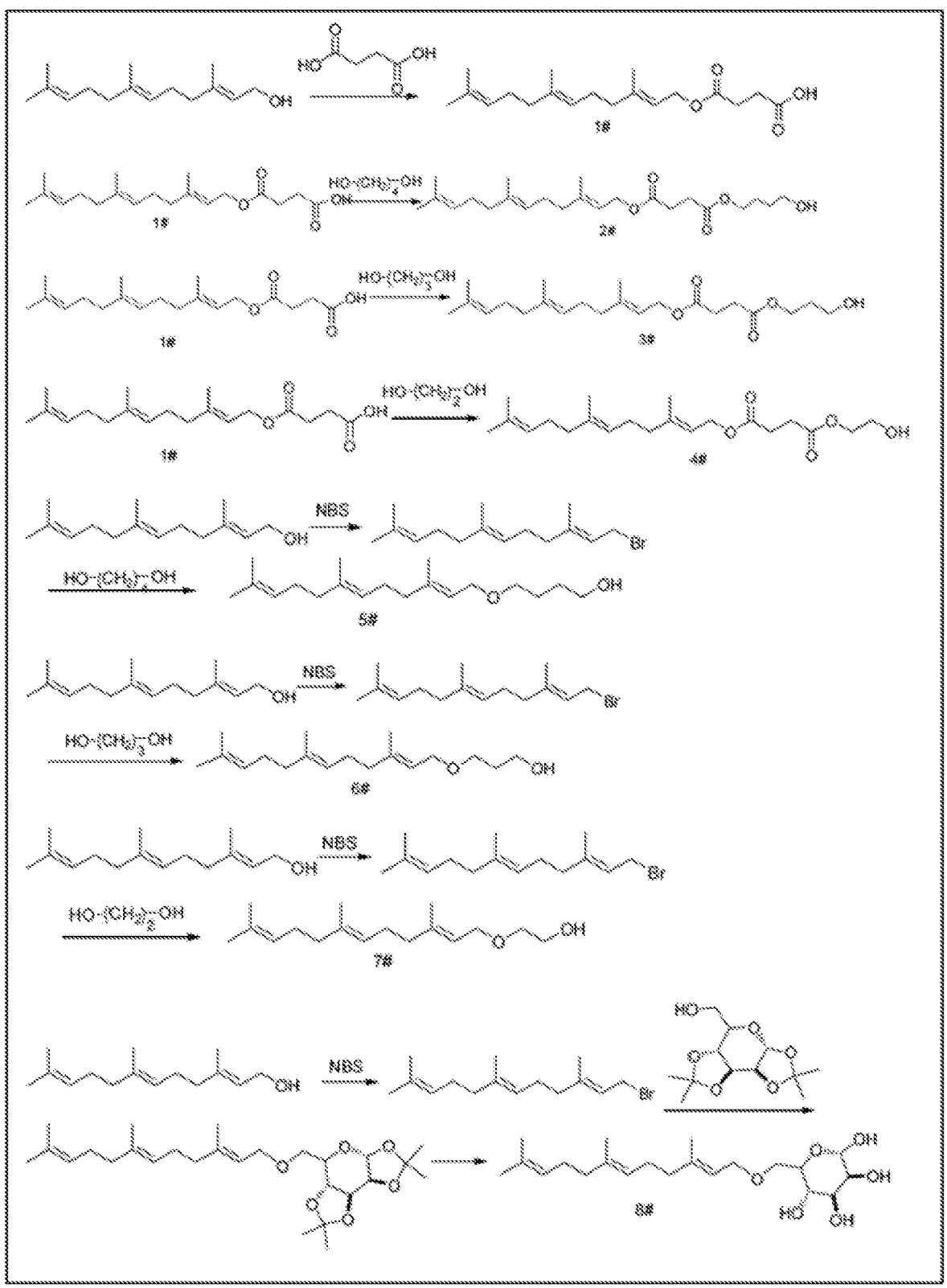
FIG. 5 shows the reaction synthesis pathways used to form the exemplary farnesol analogs according to the Examples.

Eight farnesol analogs were synthesized, the structures of which correspond to the Exemplary Farnesol Analogs 1-8 discussed above. FIG. 5 shows the reaction mechanisms utilized in the synthesis of the Exemplary Farnesol Analogs 1-8.

Table 2 shows the effect of farnesol, farnesol analogs and tyrosol analogs on the germ tube formation (GTF %) of C. albicans SC5314.

TABLE 2

| | | | GTF % (mean ± SEM, n = 2) | |
|---|---|---|---|---|
| Compounds | CAS No | MW | 100 μM | 200 μM |
| E,E-farnesol | 106-28-5 | 222.37 | 44.0 ± 3.1 | 18.4 ± 2.9 |
| trans-nerolidol | 40716-66-3 | 222.37 | 92.4* | 51.6 ± 1.8 |
| farnesyl acetate | 29548-30-9 | 264.4 | 51.9 ± 2.1 | 36.8 ± 0.8 |
| 4-hydroxy phenyl acetic acid | 156-38-7 | 152.15 | 93.1* | 86.2 ± 1.8 |
| 2-hydroxy phenyl acetic acid | 614-75-5 | 152.15 | 90.3* | 71.3 ± 2.5 |
| 3-Methoxy-4-hydroxy-phenylethyl amine | 1477-68-5 | 203.67 | 95.7* | 86.4 ± 3.3 |
| hydroxytyrosol | 10597-60-1 | 154.16 | 78.0* | 84.9 ± 0.1 |
| β-phenylethenol | 60-12-8 | 122.16 | 91.7* | 84.5 ± 0.3 |
| salidroside | 10338-51-9 | 300.3 | 93.2* | 78.0 ± 5.9 |
| #1 synthesized analog | | 322.44 | 55.9 ± 8.2 | 31.2 ± 5.0 |
| #2 synthesized analog | | 394.55 | 71.2 ± 2.9 | 33.9 ± 0.6 |
| #3 synthesized analog | | 380.52 | 66.9 ± 1.5 | 32.9 ± 1.0 |
| #4 synthesized analog | | 366.5 | 59.2 ± 4.8 | 31.1 ± 8.2 |
| #5 synthesized analog | | 294.48 | 73.8 ± 4.8 | 53.6 ± 3.0 |
| #6 synthesized analog | | 280.45 | 75.1 ± 0.5 | 51.1 ± 3.2 |
| #7 synthesized analog | | 266.42 | 72.6 ± 1.7 | 58.8 ± 2.1 |
| #8 synthesized analog | | 384.51 | 76.6 ± 0.3 | 66.3 ± 0.6 |
| Control | | | 82.8 ± 0.6 | |

*One replicate

In Vitro Screening

Caenorhabditis elegans glp4; sek1 was used as the model for in vitro screening. Breger et al. (Breger, J.; Fuchs, B. B.; Aperis, G.; Moy, T. I., Ausubel, F. M., Mylonakis, E.; "Antifungal chemical compounds identified using a C. elegans pathogenicity assay." PLoS Pathogens 3: 168-178; 2007) reported that the glp-4 mutation rendered the strain incapable of producing progeny at 25° C., and the sek-1 mutation enhanced the sensitivity of the strain to various pathogens, thereby decreasing the time for screening assays. It was observed that no progenies was produced by the Caenorhabditis elegans glp4; sek1 strain after 3 d incubation at 25° C.

The synchronization of C. elegans was achieved by collecting the eggs and arresting the larvae at L1 stage. The commonly used bleach treatment was able to release the eggs from the adult worms. However, it was observed that the released eggs were not always able to hatch after treated with sodium hypochlorite (0.2, 0.3, 0.4, 0.5, 0.7 or 1%) for 3-5 min. A modified egg laying method was developed to synchronize worms to L1 stage. In brief, stock cultures of C. elegans glp4; sek1, maintained on Nematode Growth Media plates (NGM plates), were subcultured onto NGM plates with OP 50 and incubated at 15° C. for 6-9 days. Then a chunk (1 cm$^2$) of agar with gravid adults was subcultured again onto NGM plates with OP50 and incubated at 15° C. After incubation of 3-7 days, the worms were gently washed off with 3 ml of M 9 buffer on the rotating platform (100 rpm). The plate was tilted on its lid to allow the liquid and worms drain to one side of the plate. The liquid and worms were aspirated off. The plate was washed again with M9 buffer three more times to remove OP50 as much as possible. After washing, the plate was incubated at 25° C. overnight to let the eggs hatch overnight. Since there was no OP50, the larvae were arrested at the L1 stage. The live C. elegans glp4; sek1 was quite curvy; whereas the dead C.

*elegans* glp4; sek1 tended to be straight, and in most cases the dead worms with the hyphae of *C. albicans* pieced through the body. The curvy shape and movement after shaking were used as the criteria for live.

Results from initial screening showed that the death rate of *C. elegans* glp4; sek1 infected with *C. albicans* SC5314 increased over time (Table 3). The presence of 0.4 mM farnesol reduced the death rate slightly. The higher concentration of farnesol resulted in higher death rate of the worm. This implies that the farnesol at higher concentrations may be toxic to the worm.

Table 3 shows the death rate of *C. elegans* glp 4; sek 1 infected with *C. albicans* SC5314 during incubation in 96 well plates

TABLE 3

| Compounds | Concentration | % change in the death rate compared to the control | | |
|---|---|---|---|---|
| | | day 1 | day 4 | day 5 |
| farnesol | 0.4 mM | −4 | −16 | −19 |
| | 1 mM | −12 | 14 | 10 |
| | 2 mM | −8 | 19 | 8 |
| | 3 mM | −21 | 23 | 12 |
| Death rate of control (%) | | 39 | 72 | 81 |

Seven farnesol analogs at various concentrations were screened in vitro (Table 4). Analog #1, at concentrations of 0.4 mM to 2 mM, significantly reduced the death rate of *C. elegans* glp4; sek1 infected with *C. albicans* SC5314; however, Analog #1 increased the death rate when it was 3 mM. Analogs #2, at concentrations of 0.4 mM to 3 mM, also reduced the death rate significantly. The other three synthesized analogs (#3, #4 and #5) did not have significant effect on the death of the worms. Trans-nerolidol and farnesyl acetate, at the tested four concentrations, however, increased the death rate of the worm significantly. Table 4 shows the death rate of *C. elegans* glp4; sek1 infected with *C. albicans* SC 5314 in the presence of farnesol analogs in the 96 well plates at 25° C.

TABLE 4

| Farnesol analogs | Concentration | % change in the death rate compared to the control | |
|---|---|---|---|
| | | 4 days | 5 days |
| #1 synthesized analog | 0.4 mM | −43 ± 8 | −30 ± 2 |
| | 1.0 mM | −33 ± 5 | −29 ± 11 |
| | 2.0 mM* | −23 ± 4 | −34 ± 11 |
| | 3.0 mM | 20 ± 3 | 10 ± 9 |
| #2 synthesized analog | 0.4 mM | −36 ± 4 | −38 ± 2 |
| | 1.0 mM | −28 ± 5 | −29 ± 10 |
| | 2.0 mM* | −39 ± 11 | −39 ± 11 |
| | 3.0 mM | −40 ± 0 | −40 ± 4 |
| #3 synthesized analog | 0.4 mM | −6 ± 7 | 10 ± 3 |
| | 1.0 mM | 1 ± 6 | 3 ± 8 |
| | 2.0 mM | −12 ± 9 | 9 ± 10 |
| | 3.0 mM | −2 ± 2 | 7 ± 1 |
| #4 synthesized analog | 0.4 mM | 8 ± 8 | 7 ± 1 |
| | 1.0 mM | −3 ± 3 | −1 ± 4 |
| | 2.0 mM | 4 ± 8 | 8 ± 11 |
| | 3.0 mM | 7 ± 4 | 10 ± 5 |
| #5 synthesized analog | 0.4 mM | −3 ± 6 | −6 ± 3 |
| | 1.0 mM | 2 ± 3 | 9 ± 1 |
| | 2.0 mM | −8 ± 1 | 2 ± 2 |
| | 3.0 mM | −4 ± 4 | 4 ± 1 |

TABLE 4-continued

| Farnesol analogs | Concentration | % change in the death rate compared to the control | |
|---|---|---|---|
| | | 4 days | 5 days |
| trans-nerolidol | 0.4 mM | 11 ± 4 | 4 ± 5 |
| | 1.0 mM | 3 ± 7 | −8 ± 5 |
| | 2.0 mM | 25 ± 10 | 10 ± 2 |
| | 3.0 mM | 7 ± 0 | 9 ± 9 |
| farnesyl acetate | 0.4 mM | 10 ± 6 | 4 ± 3 |
| | 1.0 mM | 27 ± 7 | 15 ± 7 |
| | 2.0 mM | 21 ± 5 | 9 ± 2 |
| | 3.0 mM | 24 ± 9 | 7 ± 10 |

Note:
results are average of two replicates except those indicted by * that are mean of three replicates The toxicity of the selected compounds/products were tested using the *C. elegans* glp4; sek1 fed on *E. coli* OP50 (Table 5). The results showed that trans-nerolidol and farnesyl acetate at 2 mM was toxic to the worm, which may explain why those two compounds increased the death rate of *C. elegans*. The five synthesized analogs at 2 mM showed no toxicity against *C. elegans*. The death rate of 2 mM farnesol was slightly higher than the control. Table 5 shows the death rate of *C. elegans* glp4; sek1 fed on *E. coli* OP50 in the presence of screened compounds at 25° C.

TABLE 5

| Compounds/products | Concentration | Death rate (%) |
|---|---|---|
| Control | / | 4 ± 0.6 |
| farnesol | 2 mM | 7 |
| farnesyl acetate | 2 mM | 12 |
| trans-nerolidol | 2 mM | 23 |
| #1 synthesized analog | 2 mM | 3.3 ± 1.2 |
| #2 synthesized analog | 2 mM | 4 ± 0.6 |
| #3 synthesized analog | 2 mM | 6 |
| #4 synthesized analog | 2 mM | 2 |
| #5 synthesized analog | 2 mM | 4 |

Note:
Results of Control, #1 and #2 products were mean of three replicates, results of others were single measurement.

Water soluble products were synthesized and had inhibitory effect on the quorum sensing of *C. albicans* in vitro.

Experimental

1. Maintenance of *Candida albicans* SC 5314

*Candida albicans* SC 5314 was streaked onto YPD agar (YPDA) and incubated at 30° C. overnight. Single colonies were subcultured in YPD broth (YPDB) and incubated 30° C., 200 rpm overnight. Glycol stocks of overnight culture in YPDB were prepared, and stored in −20° C.

2. Maintenance of *Caenorhabditis elegans*

*Caenorhabditis elegans* glp4; sek1 was maintained by subculturing on *E. coli* OP50 on NGM plates at 15° C. for 7 days. Those can be stored at 15° C. for up to 2 months.

3. In Vitro Screening of Compounds

The in vitro screening assay was based on the N-acetyl-glucosamine (GlcNAc)-triggered differentiation assay (Hornby et al., "Quorum sensing in the dimorphic fungus *Candida albicans* is mediated by farnesol;" Applied and Environmental Microbiology 67:2982-2992; 2001), which included 0.56 ml of 0.1 M imidazole buffer (pH 6.5), 0.15 ml of 0.1 M MgSO$_4$, 0.13 ml of 0.1 M GlcNAc, and 4.16 ml of sterilized water. Bioassays of quorum sensing candidates were conducted by the addition of the chemical, as a solution in 100% methanol, to the bioassay media; the final concentration of methanol was no greater than 1%.

4. In Vitro Screening of Compounds

The In vitro screening assay, based on the method of Tampakakis et al (Tampakakis, E.; Okoli, I.; Mylonakis, E.; "A C. elegans-based, whole animal, in vivo screen for the identification of antifungal compounds." Nature Protocols 3:1925-1931; 2008), is described as follows:
  a) Preparation of Worms
  L1 worms, which were prepared by the modified egg-laying method, were collected by centrifugation at 675 g for 30 s at room temperature, and the supernatant was removed. Worms were resuspended in M 9 buffer and inoculated on NGM agar plates with OP50, ~1000 worms per plate. After 2-3 days incubation at 25° C., the worms were washed off with M 9 buffer for the in vitro screening assay.
  b) Preparation of C. albicans
  Stock cultures of C. albicans SC 5314 was subcultured into 3 ml of YPD broth and incubated at 30° C. Then the overnight culture in broth was spread onto YPD agar, and incubated at 30° C. The 24 h old lawn of SC5314 was used to feed worms for 2 h at 25° C. The control were worms fed on OP50.
  c) In Vitro Screening Assay
  The worms were washed off the YPD plates and washed twice with M9 buffer. The worms were resuspended in screening media, M9 buffer with 0.3% Tween 80. The worm suspension (50 µl) was dispensed into the wells of 96-well plates, 20-30 worms/well. Aliquots (50 µl) of compounds in screening media were added to wells, 5 wells each compound. The 96 well plates were incubated at 25° C. for up to 5 days. Live and dead worms were counted during incubation, and the death rates of worms were calculated.

While the invention has been described in detail with respect to the specific embodiments thereof, it will be appreciated that those skilled in the art, upon attaining an understanding of the foregoing, may readily conceive of variations and equivalents to these embodiments. Accordingly, the scope of the present invention should be assessed as that of the appended claims and any equivalents thereto.

What is claimed is:

1. A web comprising a plurality of fibers, wherein the web comprises a treatment composition, the treatment composition comprising a farnesol analog comprising a hydrophilic end group attached to farnesol via a covalent linkage, wherein the hydrophilic end group defines a hydroxyl end group or a carboxylic acid end group, and wherein the covalent linkage comprises an ester group or an ether group.

2. The web according to claim 1, wherein the covalent linkage comprises at least one ester group.

3. The web according to claim 2, having the structure:

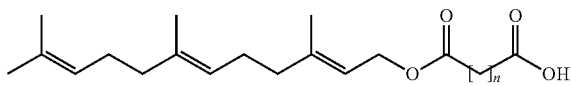

where n is an integer from 1 to about 8, or its deprotonated salt.

4. The web according to claim 3, wherein n is 2, 3, or 4.

5. The web according to claim 2, wherein the hydrophilic end group comprises at least two ester groups.

6. The web according to claim 5, having the structure:

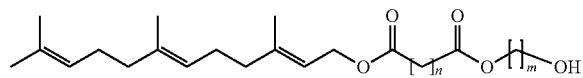

where n is an integer from 1 to about 8; and m is an integer from 1 to about 8.

7. The web according to claim 6, wherein n is 2, 3, or 4; and wherein m is 2, 3, or 4.

8. The web according to claim 1, wherein the covalent linkage comprises an ether group, and wherein the hydrophilic end group defines a hydroxyl end group.

9. The web according to claim 8, having the structure:

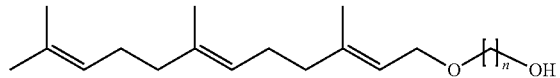

where n is an integer from 1 to about 8.

10. The web according to claim 9, wherein n is 2, 3, or 4.

11. The web according to claim 8, having the structure:

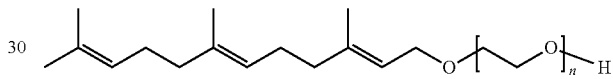

where n is an integer that is 1 to about 100.

12. The web according to claim 8, wherein the farnesol analog comprises a monosaccharide covalently attached to the farnesol via an ether linkage.

13. The web according to claim 12, having the structure:

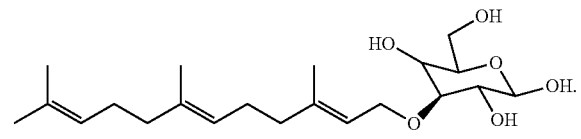

14. The web according to claim 1, wherein the farnesol analog has a solubility in water that is 10 grams per 100 grams of water or greater.

15. A wipe comprising the web according to claim 1.

16. An absorbent article comprising:
  a liquid impermeable outer cover;
  a liquid permeable bodyside liner, wherein the bodyside liner comprises the web according to claim 1;
  an absorbent body disposed between the outer cover and bodyside liner.

17. A method of forming a web coated with a treatment composition, comprising
  forming a treatment composition comprising a farnesol analog that is soluble in water from a farnesol molecule having a hydroxyl group, the method comprising:
  covalently attaching a hydrophilic end group to the farnesol molecule via reaction with its hydroxyl group to form a covalent linkage, wherein the hydrophilic end group defines a hydroxyl end group or a carboxylic acid end group, and wherein the covalent linkage comprises an ester group or an ether group; and
  applying the treatment composition to the web.

18. The method as in claim 17, wherein the covalent linkage comprises an ester group formed via an esterification reaction between the hydroxyl group of the farnesol molecule and a carboxylic acid functional molecule.

19. The method as in claim 18, wherein the carboxylic acid functional molecule is a dicarboxylic acid such that the hydrophilic end group defines a carboxylic acid end group upon reaction of the dicarboxylic acid with the hydroxyl group of the farnesol molecule.

20. The method as in claim 19, further comprising:
   reacting the carboxylic acid end group with a glycol via a second esterification reaction to form a farnesol analog having a hydroxyl group covalently attached via two ester linkages.

21. The method as in claim 20, wherein the glycol is selected from the group consisting of ethylene glycol, propylene glycol, and butane-1,4-diol.

22. The method as in claim 17, wherein the covalent linkage comprises an ether group formed by reacting farnesol with an alcohol via a dehydration reaction to form the ether group.

23. The method as in claim 22, wherein the alcohol is a glycol selected from the group consisting of ethylene glycol, propylene glycol, and butane-1,4-diol.

24. The method as in claim 22, wherein the hydrophilic end group comprises a sugar.

* * * * *